United States Patent [19]

Nojiri et al.

[11] 4,414,135

[45] Nov. 8, 1983

[54] SILVER-BASED CATALYST CONTAINING BROMINE AND/OR FLUORINE AS AN ANIONIC COMPONENT FOR THE PRODUCTION OF ETHYLENE OXIDE

[75] Inventors: Naohiro Nojiri; Yukio Sakai, both of Ami, Japan

[73] Assignee: Mitsubishi Petrochemical Co. Ltd., Tokyo, Japan

[21] Appl. No.: 349,977

[22] Filed: Feb. 18, 1982

[30] Foreign Application Priority Data

Apr. 30, 1981 [JP] Japan ................................. 56-65435

[51] Int. Cl.$^3$ .......................... B01J 27/08; B01J 27/12
[52] U.S. Cl. ..................................... 502/224; 549/200
[58] Field of Search ......................................... 252/441

[56] References Cited

U.S. PATENT DOCUMENTS

| | | | |
|---|---|---|---|
| 2,615,900 | 10/1952 | Sears | 252/441 X |
| 2,799,687 | 7/1957 | Gould et al. | 252/441 X |
| 3,132,157 | 5/1964 | Endler et al. | 252/441 X |
| 3,637,629 | 1/1972 | Dorfman et al. | 252/441 X |

*Primary Examiner*—Patrick Garvin
*Attorney, Agent, or Firm*—Sherman & Shalloway

[57] ABSTRACT

A catalyst comprising sodium and cesium as a cationic component and at least one of bromine and fluorine as an anionic component in addition to silver which is a typical conventional catalyst component for the production of ethylene oxide by oxidation of ethylene. Use of the catalyst of the invention gives ethylene oxide at an improved selectivity.

8 Claims, No Drawings

SILVER-BASED CATALYST CONTAINING BROMINE AND/OR FLUORINE AS AN ANIONIC COMPONENT FOR THE PRODUCTION OF ETHYLENE OXIDE

BACKGROUND OF THE INVENTION

This invention relates to a process for the production of ethylene oxide by oxidizing ethylene, and to a catalyst therefor. It is based on the new discovery that a combination of sodium, cesium and bromine and/or fluorine with silver provides a catalyst having increased performance in the oxidation of ethylene. Bromine and/or fluorine will be referred to as "halogen" hereinafter.

A silver catalyst is substantially the sole catalyst component used in the industrial production of ethylene oxide by the oxidation of ethylene with molecular oxygen. Silver alone, however, did not prove to be a perfect industrial catalyst, and efforts have been made to increase its performance by including various additives (for example, U.S. Pat. Nos. 2,238,471, 2,404,438, 2,671,764 and 2,799,687). Many of these efforts have been directed to the addition of alkali metals (for example, British Pat. No. 1,413,251 and U.S. Pat. No. 4,212,772). Usually, halogen compounds of these metals are excluded because they are a poison to silver.

The present invention have made extensive investigations about the effects of anionic components as well as alkali metals as cationic components. These investigations have led to the discovery that the use of the aforesaid specified halogen elements (to be referred to simply as a halogen element), previously believed to have a poisonous action, in combination with sodium and cesium unexpectedly gives a catalyst having greatly increased performance.

SUMMARY OF THE INVENTION

According to this invention, there is provided a catalyst for the production of ethylene oxide by oxidation of ethylene, comprising (A) silver, (B) (1) more than 1000 ppm (mg/kg of the catalyst) of sodium, and (2) cesium as a cationic component, and (C) bromine and/or fluorine as an anionic component.

In another aspect, there is provided a process for producing ethylene oxide, which comprises contacting ethylene and a gas containing molecular oxygen with the aforesaid catalyst at a temperature of 180° to 300° C. and a pressure of 1 to 35 kg/cm$^2$.

DETAILED DESCRIPTION OF THE INVENTION

In the preparation of the catalyst of this invention, a sodium compound to be added is preferably in the form of sodium carbonate, sodium bicarbonate or sodium nitrate. It may, however, be in the form of a hydroxide, nitrite, sulfate, borate, silicate, phosphate, halide or carboxylate (e.g., sodium acetate or sodium oxalate), or a mixture of any of these compounds with sodium carbonate or sodium bicarbonate.

A cesium compound to be added is preferably in the form of a chloride, bromide and/or fluoride depending upon the type of the halogen element to be added to the catalyst. It may be added in the form of any of the water-soluble or water-insoluble compounds such as its hydroxide or salts such as the nitrate, nitrite, carbonate and sulfate.

Sources of the halogen may be sodium bromide and/or fluoride or cesium bromide and/or fluoride which are salts of Br and/or F with sodium or cesium, or other salts such as BaBr$_2$, BaF$_2$, KBr, KF, RbBr, RbF, LiBr and LiF.

In any case, it is essential to add sodium, cesium and bromine and/or fluorine as well as silver, and a combination of these gives a catalyst having greatly increased performance.

The amount of sodium added is more than 1000 ppm (mg/kg of catalyst) based on the catalyst. Preferably, it is from 1100 ppm to 1.50% by weight, more preferably 1200 ppm to 1% by weight. Advantageously, the amount of sodium added ranges from 1300 ppm to 5000 ppm. Preferably, the amount of sodium is such that the atomic ratio of Na to Ag is not more than 0.58, especially not more than 0.45. When the amount of sodium is too large, both the activity and selectivity of the catalyst are reduced. When it is too small, the dispersion of silver particles on a carrier is worese than that in the catalyst of this invention as observed by a scanning electron microscospe; hence, the activity of the catalyst is low and a higher bath temperature is required in order to obtain the same activity, with the consequence that the effect of adding halogen is not fully produced.

The suitable amount of cesium added is smaller than that of sodium. It is generally from 10 ppm to 0.5% by weight, preferably from 15 ppm to 0.1% by weight, based on the catalyst. If the amount is too large, the activity of the catalyst is markedly decreased, and if it is too small, the effect of the halogen element is not fully produced.

The suitable amount of bromine and/or fluorine to be added to the catalyst of this invention is from 5 ppm to 0.1% by weight, preferably from 7 ppm to 0.07% by weight. The addition of too large an amount results in the exhibition of its poisoning action and causes a drastic reduction in the performance of the catalyst. Thus, the characteristic feature of the invention is that bromine and/or fluorine previously believed to have a poisoning action has been found to have an action of a performance improver by adding it in a very small amount in combination with sodium and cesium.

Bromine and/or fluorine may be used singly or as a mixture, and each of them may be used together with chlorine.

In the catalyst of this invention, the cationic component is not limited to sodium and cesium, and a small amount of a third component such as lithium, barium, rubidium, potassium and thallium may be added together.

The above catalyst components are used in the form of a supported catalyst mainly from the standpoint of economy and active lifetime. A porous refractory material is used as a carrier. Desirably, the carrier has a BET surface area of 0.05 to 10 m$^2$/g and an apparent porosity of at least 15%. A carrier composed of alpha-alumina as a main component (a so-called alundum carrier) is preferred.

Deposition of sodium, cesium and halogen may be effected by dissolving or dispersing the aforesaid compounds of these ingredients in an aqueous solvent, impregnating a carrier with the resulting solution or dispersion, and drying the impregnated carrier under heat in the presence of a gas such as nitrogen or air. Sodium, cesium and halogen may be deposited simultaneously or separately in any desired stage of catalyst preparation in various modes. For example, similar effects can be obtained by performing the deposition before, during or after the impregnation of the silver compound.

Deposition of silver can be carried out by dipping a carrier molded in a suitable form such as spheres, pellets or rings in an aqueous solution or dispersion prepared by dissolving or dispersing a silver compound such as silver oxalate, silver nitrate or silver lactate in water in the presence or absence of a solubilizing agent such as ethylenediamine, drying the impregnated carrier, and calcining it at a suitable temperature in a stream of a gas such as nitrogen, air or hydrogen. The kind of the gas and the temperature in the calcination are selected depending upon the kind of the silver salt, etc. The calcination temperature is usually 100° to 1000° C., preferably 150° to 700° C. The amount of silver supported in the catalyst is usually 1 to 25% by weight, preferably 3 to 20% by weight, based on the catalyst.

The silver-based catalyst of this invention is used conveniently in the production of ethylene oxide by the oxidation of ethylene in the vapor phase with molecular oxygen. The reaction conditions for the oxidation of ethylene are known, and broadly described in the prior art literature. In the production of ethylene oxide in the presence of the silver-based catalyst of this invention, the reaction pressure is 1 to 35 kg/cm$^2$, preferably 5 to 20 kg/cm$^2$; the reaction temperature is 180° to 300° C., preferably 190° to 260° C.; ethylene is used in an amount of 1 to 40% by volume, preferably 15 to 35% by volume; and oxygen is used in an amount of 1 to 20% by volume, preferably 5 to 10% by volume, diluted with a diluting agent such as methane and nitrogen, preferably methane, in an amount of 20 to 70% by volume, preferably 30 to 65% by volume. Oxygen may be supplied in the form of air or industrial oxygen. Preferably, a reaction inhibitor such as a halogenated hydrocarbon is added to the starting gaseous mixture. In particular, by adding several ppm to several ten ppm (by weight) of ethylene dichloride, vinyl chloride, etc. to the starting gas, the formation of hot spots in the catalyst can be prevented and the properties, especially the selectivity, of the catalyst can be greatly improved. The starting gaseous mixture is continuously introduced into a reactor filled with the catalyst. The resulting ethylene oxide is separated and recovered from the reaction mixture by using customary methods.

The following examples illustrate the present invention more specifically.

EXAMPLE 1

Thirty grams of an alpha-alumina carrier (SA 5561) was dipped in 50 ml of an aqueous solution containing 2.0 g of sodium carbonate. Excess solution was removed by filtration, and the dipped carrier was dried at 110° C. for 2 hours in a stream of nitrogen gas to prepare a sodium carbonate-impregnated carrier.

Silver nitrate (6.0 g) and 3.4 g of potassium oxalate ($K_2C_2O_4.H_2O$) were each dissolved in 100 ml of water. The resulting aqueous solutions were then mixed, and heated in a water bath at 60° C. to obtain a white precipitate of silver oxalate. Potassium was removed from the precipitate by repeating centrifugation and washing with distilled water. Separately, 6.6 ml of a 1:1 mixture of ethylenediamine and water was prepared, and with ice cooling, the silver oxalate precipitate was gradually dissolved in the mixture to prepare a silver solution. The above carrier was dipped in the resulting solution. The excess solution was allowed to flow out, and the dipped carrier was dried at 80° C. under reduced pressure in a rotary evaporator. The dried carrier was transferred to a calcination tube, and the temperature was raised in a nitrogen stream over the course of 2 hours to 300° C. at which it was calcined for an additional 2 hours. The calcined product was cooled, and dipped in 50 ml of a methanol/water mixture (water content 0.3% by weight) containing 0.05 g of CsBr. The excess solution was removed by filtration, and the dipped product was dried at 110° C. for 2 hours in a stream of nitrogen gas to prepare a supported catalyst of this invention containing 8% by weight of Ag, 0.35% by weight of Na, 126 ppm of Cs and 76 ppm of Br.

The resulting catalyst was pulverized to a size of 9 to 28 mesh, and 10 g of the pulverized catalyst was filled in a steel reaction tube having an inside diameter of 20 mm. A gaseous mixture consisting of 30% by volume ethylene, 8% by volume of oxygen, 2 ppm of vinyl chloride and the balance being methane was passed through the reaction tube at a pressure of 9 kg/cm$^2$ and an SV of 2000$^{-1}$. At a bath temperature of 213° C., an oxygen conversion of 30% and an ethylene oxide selectivity of 81% were obtained. During the 3-week operating period, no change in the performance of the catalyst was noted.

EXAMPLE 2

A supported catalyst containing 8.0% of Ag, 0.35% by weight of Na, 126 ppm of Cs and 18 ppm of F was prepared in the same way as in Example 1 except that 0.036 g of CsF was used instead of CsBr. The catalyst was tested under the same reaction conditions as in Example 1. At a reaction temperature of 216° C., the results shown in Table 1 were obtained.

EXAMPLE 3

A supported catalyst containing 7.2% by weight of Ag, 0.19% by weight of Na, 126 ppm of Cs and 76 ppm of Br was prepared in the same way as in Example 1 except that 2.0 g of sodium bicarbonate was used instead of sodium carbonate. The catalyst was tested under the same reaction conditions as in Example 1. At a reaction temperature of 217° C., the results shown in Table 1 were obtained.

EXAMPLE 4

A supported catalyst containing 8.0% by weight of Ag, 0.35% by weight of Na, 126 ppm of Cs, 37 ppm of K and 18 ppm of F was prepared in the same way as in Example 1 except that 0.014 g of KF and 0.046 g of CsNO$_3$ were used instead of CsBr. The catalyst was tested under the same conditions as in Example 1. At a reaction temperature of 217° C., the results shown in Table 1 were obtained.

TABLE 1

| Example | Composition of the catalyst | Raw materials added | Oxygen conversion (%) | Selectivity (%) |
|---|---|---|---|---|
| 1 | Ag—Na—Cs—Br<br>8.0  0.35  126  76<br>wt%  wt%  ppm  ppm | Na$_2$CO$_3$, CsBr | 30 | 81 |
| 2 | Ag—Na—Cs—F<br>8.0  0.35  126  18<br>wt%  wt%  ppm  ppm | Na$_2$CO$_3$, CsF | 30 | 82 |
| 3 | Ag—Na—Cs—Br<br>7.2  0.19  126  76 | NaHCO$_3$, CsBr | 30 | 82 |

TABLE 1-continued

| Example | Composition of the catalyst | Raw materials added | Oxygen conversion (%) | Selectivity (%) |
|---|---|---|---|---|
| 4 | Ag—Na—Cs—K—F<br>8.0 0.35 126 37 18<br>wt wt ppm ppm ppm<br>% % | Na₂CO₃,<br>KF,<br>CsNO₃ | 30 | 81 |

COMPARATIVE EXAMPLES 1 TO 5

Five different catalysts having the compositions shown in Table 2 were prepared in the same way as in Example 1. These catalysts were each tested under the same reaction conditions as in Example 1 except that the oxygen conversion was set at 50%.

The results are shown in Table 2 together with those obtained in Example 2. It is seen that the selectivity of the catalyst of this invention is superior.

TABLE 2

| Runs | Composition of the catalyst | Raw materials added | Oxygen conversion (%) | Selectivity (%) |
|---|---|---|---|---|
| Example 2 | Ag—Na—Cs—F<br>8.0 0.35 126 18<br>wt wt ppm ppm<br>% % | Na₂CO₃,<br>CsF | 50 | 79 |
| Comparative Example | | | | |
| 1 | Ag—Na<br>8.0 0.35<br>wt wt<br>% % | Na₂CO₃ | 50 | 72.8 |
| 2 | Ag—Cs—Br<br>8.0 126 76<br>wt ppm ppm<br>% | CsBr | 50 | 70.3 |
| 3 | Ag—Na—Cs—I<br>8.0 0.35 126 120<br>wt wt ppm ppm<br>% % | Na₂CO₃,<br>CsI | 50 | 60 |
| 4 | Ag—Na—Cs—Br<br>8.0 0.01 50 30<br>wt wt ppm ppm<br>% % | Na₂CO₃,<br>CsBr | 50 | 74.5 |
| 5 | Ag—Na—Cs—F<br>8.0 0.01 50 7<br>wt wt ppm ppm<br>% % | Na₂CO₃,<br>CsF | 50 | 74.0 |

EXAMPLE 5

A supported catalyst comprising 8.4% by weight of Ag, 2500 ppm of Na, 160 ppm of Cs, 21 ppm of Cl and 47 ppm of Br was prepared in the same way as in Example 1 except that sodium bicarbonate was used instead of sodium carbonate and that cesium bromide and cesium chloride were used instead of cesium bromide, and tested under the same reaction conditions as in Example 1. At a reaction temperature of 220° C., an oxygen conversion of 40% and a selectivity of 81.1% were obtained.

EXAMPLE 6

A supported catalyst comprising 8.4% by weight of Ag, 2500 ppm of Na, 160 ppm of Cs, 47 ppm of Br and 11 ppm of F was prepared in the same way as in Example 5, and tested under the same reaction conditions as in Example 1. At a reaction temperature of 216° C., an oxygen conversion of 30% and a selectivity of 82.5% were obtained.

What we claim is:

1. A catalyst for the production of ethylene oxide by oxidation of ethylene, said catalyst comprising
   (A) silver,
   (B) (1) sodium in an amount of more than 1000 ppm (mg/kg of catalyst) based on the catalyst and (2) cesium as a cationic component, the amount of cesium being smaller than that of sodium and ranging from 10 ppm to 0.5% by weight based on the catalyst, and
   (C) at least one halogen element selected from bromine and fluorine as an anionic component, the amount of the halogen element being from 5 ppm to 0.1% by weight based on the catalyst.

2. The catalyst of claim 1 wherein the amount of sodium is in the range of from 1100 ppm to 1.50% by weight based on the catalyst.

3. The catalyst of claim 1 wherein the amount of sodium is in the range of from 1200 ppm to 1% by weight based on the catalyst.

4. The catalyst of claim 1, 2 or 3 wherein the amount of cesium is in the range of from 15 ppm to 0.1% by weight based on the catalyst.

5. The catalyst of claim 1, 2 or 3 wherein the amount of at least one of halogen element is in the range of from 7 ppm to 0.07 by weight based on the catalyst.

6. The catalyst of claim 1, 2 or 3 wherein silver, sodium, cesium and bromine and/or fluorine as catalyst ingredients are supported on a porous refractory carrier having a surface area of 0.05 to 10 m²/g and an apparent porosity of at least 15%.

7. The catalyst of claim 1, 2 or 3 wherein the atomic ratio of sodium to silver is not more than 0.58.

8. The catalyst of claim 1, 2 or 3 wherein the amount of silver in the catalyst is from 1 to 25% by weight, based on the catalyst.

* * * * *